(12) United States Patent
Yamamura

(10) Patent No.: US 11,957,315 B2
(45) Date of Patent: Apr. 16, 2024

(54) SIGNAL PROCESSING DEVICE, ENDOSCOPE SYSTEM, AND SIGNAL PROCESSING METHOD

(71) Applicant: OLYMPUS CORPORATION, Hachioji (JP)

(72) Inventor: Daiki Yamamura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 71 days.

(21) Appl. No.: 17/902,293

(22) Filed: Sep. 2, 2022

(65) Prior Publication Data

US 2022/0409031 A1 Dec. 29, 2022

Related U.S. Application Data

(63) Continuation of application No. PCT/JP2020/009792, filed on Mar. 6, 2020.

(51) Int. Cl.
*A61B 1/045* (2006.01)
*A61B 1/00* (2006.01)
*H04N 23/60* (2023.01)

(52) U.S. Cl.
CPC ............ *A61B 1/045* (2013.01); *H04N 23/60* (2023.01); *A61B 1/00009* (2013.01)

(58) Field of Classification Search
CPC ...... H04N 23/60; H04N 23/665; A61B 1/045; A61B 1/00009
See application file for complete search history.

(56) References Cited

U.S. PATENT DOCUMENTS

| 9,319,603 | B2 | 4/2016 | Dai et al. |
| 10,653,304 | B2* | 5/2020 | Matsui ............... A61B 1/0655 |
| 11,671,552 | B2* | 6/2023 | Koyama ............... H04N 7/18 |
| | | | 348/500 |
| 11,765,478 | B2* | 9/2023 | Saito ................. H03L 7/104 |
| | | | 375/376 |
| 2012/0320177 | A1 | 12/2012 | Nishimura et al. |
| 2013/0083178 | A1 | 4/2013 | Kotani et al. |

(Continued)

FOREIGN PATENT DOCUMENTS

| JP | 3-114432 A | 5/1991 |
| JP | 2013-454 A | 1/2013 |

(Continued)

OTHER PUBLICATIONS

International Search Report dated Jul. 14, 2020, issued in counterpart International Application No. PCT/JP2020/009792 (2 pages).

*Primary Examiner* — Brian P Yenke
(74) *Attorney, Agent, or Firm* — WHDA, LLP

(57) ABSTRACT

A signal processing device includes: a processor including at least one or more pieces of hardware, the processor being configured to: switch to one of a first state in which an input of a clock signal for operating an imager to the imager is permitted and a second state in which the input of the clock signal to the imager is prohibited, and temporarily switch from the first state to the second state when a first synchronization signal output from a first synchronization signal generation circuit and a second synchronization signal output from a second synchronization signal generation circuit are not synchronized.

15 Claims, 8 Drawing Sheets

(56) References Cited

U.S. PATENT DOCUMENTS

| | | | | |
|---|---|---|---|---|
| 2013/0329025 A1* | 12/2013 | Hashimoto | ............ | A61B 1/045 |
| | | | | 348/65 |
| 2015/0070527 A1* | 3/2015 | Yanada | .................. | H04N 25/70 |
| | | | | 348/222.1 |
| 2017/0288684 A1* | 10/2017 | Ogihara | .................. | H03L 7/095 |
| 2018/0220881 A1* | 8/2018 | Adachi | .................... | H04N 7/18 |
| 2020/0214540 A1* | 7/2020 | Tanaka | ................... | A61B 1/045 |
| 2020/0400566 A1* | 12/2020 | Talbert | .................... | G01S 17/89 |
| 2022/0322923 A1* | 10/2022 | Harada | ................ | H04N 25/745 |
| 2022/0409009 A1* | 12/2022 | Yamamura | ......... | A61B 1/00006 |

FOREIGN PATENT DOCUMENTS

| | | |
|---|---|---|
| JP | 2013-75100 A | 4/2013 |
| JP | 2015-80702 A | 4/2015 |

\* cited by examiner

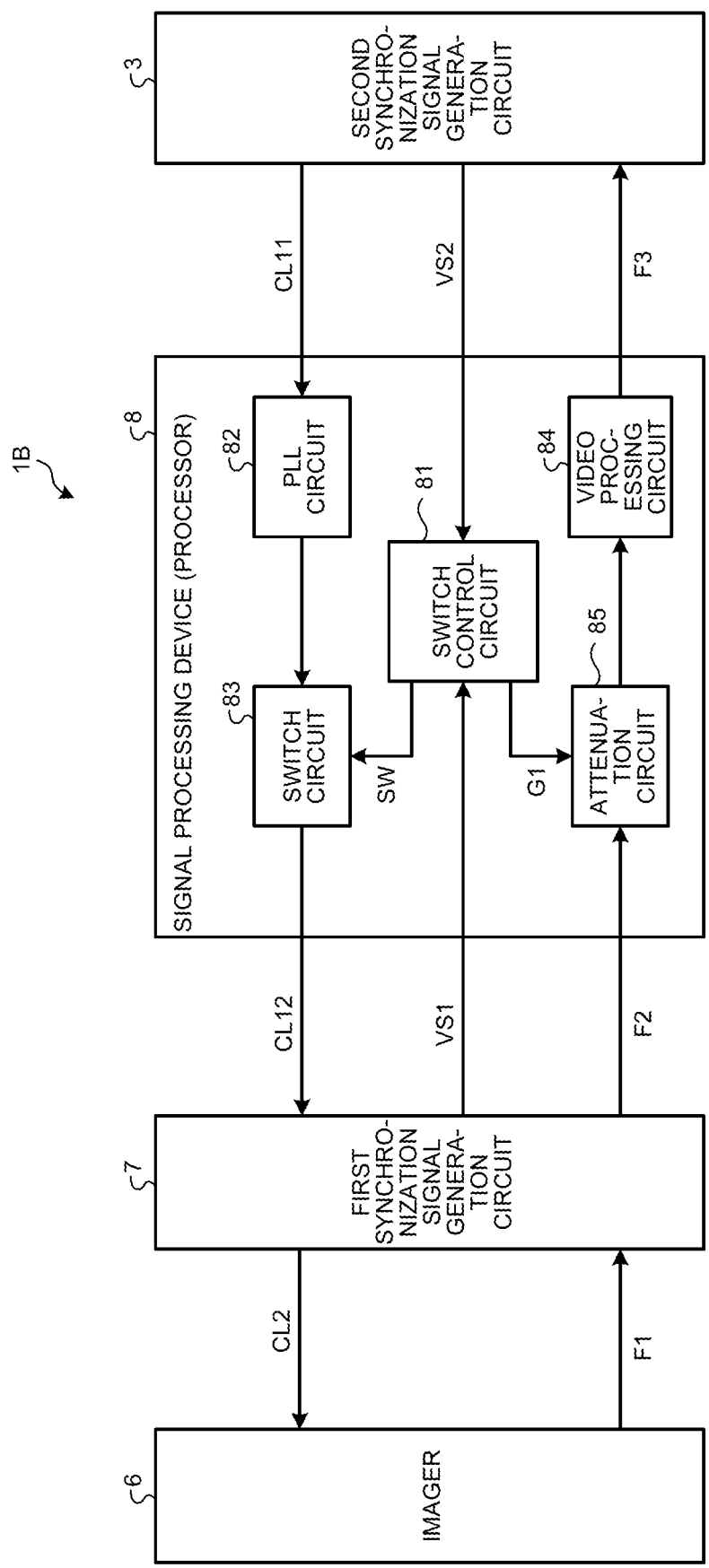

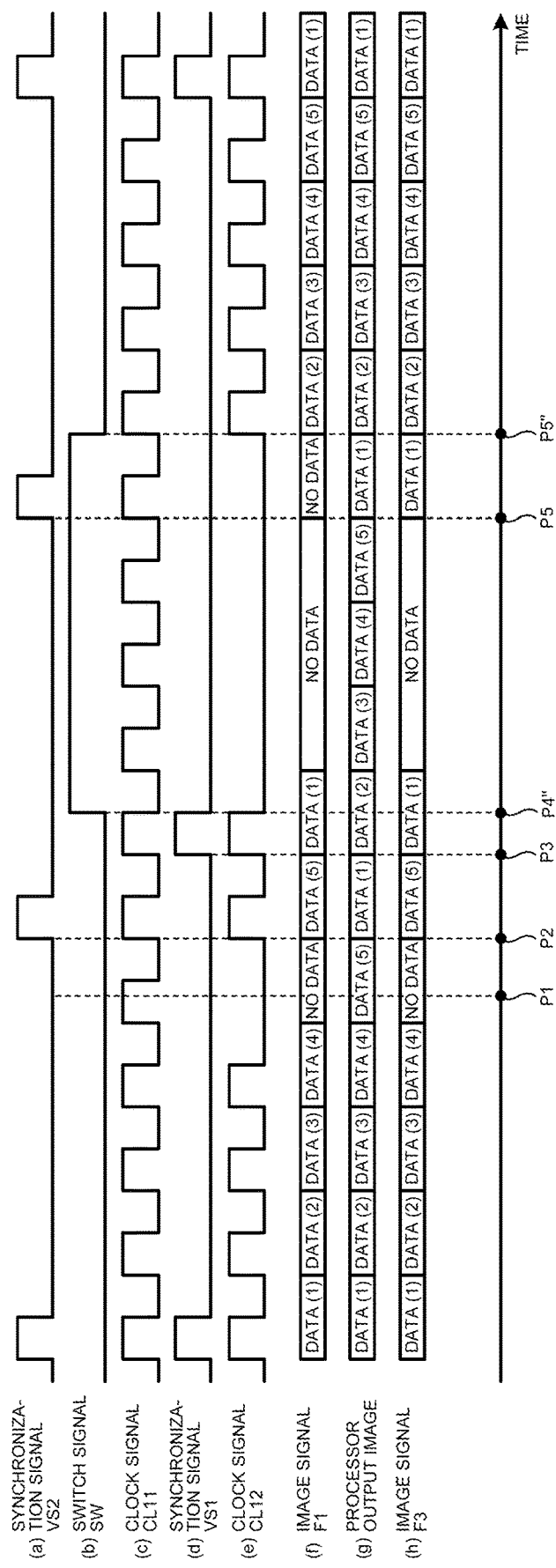

SIGNAL PROCESSING DEVICE, ENDOSCOPE SYSTEM, AND SIGNAL PROCESSING METHOD

CROSS-REFERENCE TO RELATED APPLICATION

This application is a continuation of International Application No. PCT/JP2020/009792, filed on Mar. 6, 2020, the entire contents of which are incorporated herein by reference.

BACKGROUND

1. Technical Field

The present disclosure relates to a signal processing device, an endoscope system, and a signal processing method.

2. Related Art

In the related art, there is known an endoscope system including an endoscope in which an imager is provided at a distal end and which is inserted into a subject, and a processor that processes an image signal from the imager.

In such an endoscope system, the processor outputs, to the imager, a clock signal for operating the imager and a synchronization signal (hereinafter, described as a second synchronization signal) indicating timing at which an image signal is acquired for each frame from the imager. Then, the imager operates according to the clock signal and outputs the image signal to the processor at timing based on the second synchronization signal.

Meanwhile, in recent years, in order to downsize an imager, a configuration has been proposed in which a function of transmitting and receiving a synchronization signal is removed from a function of the imager (see, for example, U.S. Pat. No. 9,319,603 B2).

In the technique described in U.S. Pat. No. 9,319,603 B2, in order to generate a synchronization signal from an image signal in an imager, a change in a voltage level is provided in the image signal. Then, in the technology, a synchronization signal generation unit that generates a first synchronization signal indicating timing at which the image signal is transmitted for each frame based on the change in the voltage level is provided, and the first synchronization signal is output from the synchronization signal generation unit to the processor.

SUMMARY

In some embodiments, a signal processing device includes: a processor including at least one or more pieces of hardware, the processor being configured to: switch to one of a first state in which an input of a clock signal for operating an imager to the imager is permitted and a second state in which the input of the clock signal to the imager is prohibited, and temporarily switch from the first state to the second state when a first synchronization signal output from a first synchronization signal generation circuit and a second synchronization signal output from a second synchronization signal generation circuit are not synchronized.

In some embodiments, an endoscope system includes: an endoscope configured to be inserted into a subject; and a processor comprising at least one or more pieces of hardware, the processor being configured to: switch to one of a first state in which an input of a clock signal for operating an imager to the imager is permitted and a second state in which the input of the clock signal to the imager is prohibited, and temporarily switch from the first state to the second state when a first synchronization signal output from a first synchronization signal generation circuit and a second synchronization signal output from a second synchronization signal generation circuit are not synchronized.

In some embodiments, provided is a signal processing method executed by a processor including at least one or more pieces of hardware. The signal processing method includes: switching to one of a first state in which an input of a clock signal for operating an imager to the imager is permitted and a second state in which the input of the clock signal to the imager is prohibited; and temporarily switching from the first state to the second state when a first synchronization signal output from a first synchronization signal generation circuit and a second synchronization signal output from a second synchronization signal generation circuit are not synchronized.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 7 is a block diagram illustrating a configuration of a main part of an endoscope system according to a third embodiment; and FIG. 8 is a view for describing a modification of the first to third embodiments.

DETAILED DESCRIPTION

Figure 1:
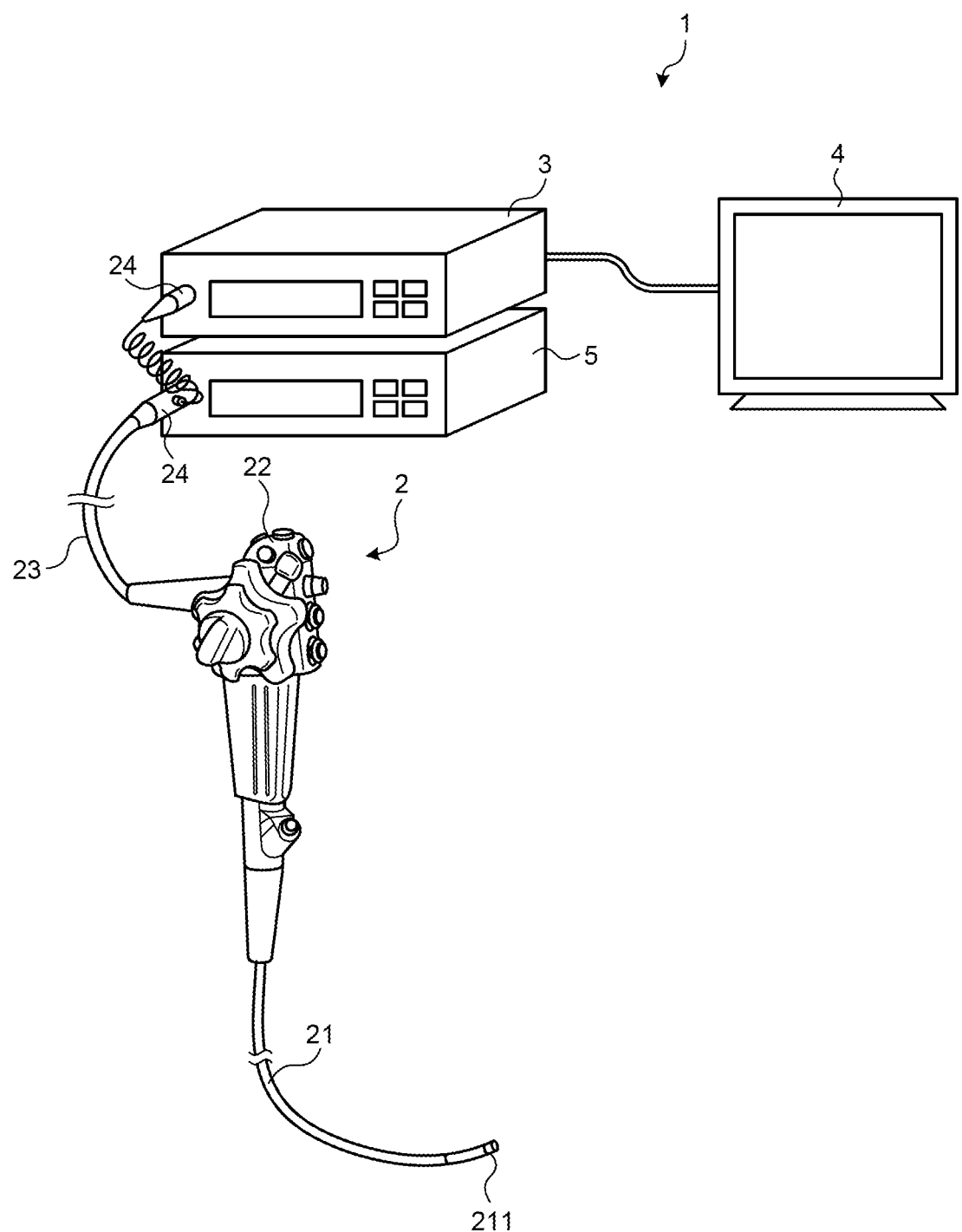
FIG. 1 is a diagram illustrating a configuration of an endoscope system according to a first embodiment.

Hereinafter, modes for carrying out the disclosure (embodiments) will be described with reference to the drawings. Note that the disclosure is not limited by the embodiments described below. Further, in the description of the drawings, the same parts will be described with the same reference numerals.

First Embodiment

Configuration of Endoscope System

FIG. 1 is a diagram illustrating a configuration of an endoscope system 1 according to the first embodiment.

The endoscope system 1 is a system that is used, for example, in a medical field and observes the inside of a subject (inside of a living body). As illustrated in FIG. 1, the endoscope system 1 includes an endoscope 2, a second synchronization signal generation circuit 3, a display device 4, and a light source device 5.

The endoscope 2 is partially inserted into the living body and captures a subject image reflected from the inside of the living body, and outputs an image signal generated by the imaging. As illustrated in FIG. 1, the endoscope 2 includes an insertion unit 21, an operating unit 22, a universal cord 23, and a connector unit 24.

The insertion unit 21 is a portion at least part of which has flexibility and that is inserted into a living body. In the insertion unit 21, an imager 6 (see FIG. 2) is provided at a distal end portion 211 (FIG. 1).

Note that a detailed configuration of the imager 6 will be described in "Configuration of main part of endoscope system" described later.

The operating unit 22 is connected to a proximal end portion of the insertion unit 21. Then, the operating unit 22 receives various operations of the endoscope 2.

The universal cord 23 is a cord extending from the operating unit 22 in a direction different from the extending direction of the insertion unit 21 and provided with a cable for transmitting the above-described image signal and the like, an optical fiber for guiding illumination light emitted from the light source device 5, and the like.

The connector unit 24 is provided at an end portion of the universal cord 23, and is detachably connected to the second synchronization signal generation circuit 3 and the light source device 5. In the first embodiment, a first synchronization signal generation circuit 7 (see FIG. 2) and a signal processing device 8 (see FIG. 2) are provided in the connector unit 24.

Note that detailed configurations of the first synchronization signal generation circuit 7 and the signal processing device 8 will be described in "Configuration of main part of endoscope system" described later.

The second synchronization signal generation circuit 3 integrally controls the entire operation of the endoscope system 1. For example, the second synchronization signal generation circuit 3 performs various types of image processes on the image signal output from the imager 6 and having passed through the insertion unit 21, the operating unit 22, the universal cord 23, and the connector unit 24.

Note that a detailed configuration of the second synchronization signal generation circuit 3 will be described in "Configuration of main part of endoscope system" described later.

The display device 4 is a liquid crystal display (LCD), an electro luminescence (EL) display, or the like, and displays an image or the like based on an image signal subjected to image processing by the second synchronization signal generation circuit 3.

The light source device 5 corresponds to a light source. The light source device 5 includes, for example, a halogen lamp, a white light emitting diode (LED), and the like, and emits illumination light. Then, the illumination light emitted from the light source device 5 passes through the connector unit 24, the universal cord 23, the operating unit 22, and the insertion unit 21, and then is emitted from the distal end portion 211 of the insertion unit 21 toward the inside of the living body.

Configuration of main part of endoscope system Next, configurations of the imager 6, the first synchronization signal generation circuit 7, the signal processing device 8, and the second synchronization signal generation circuit 3 which are main parts of the endoscope system 1 will be described.

Figure 2:
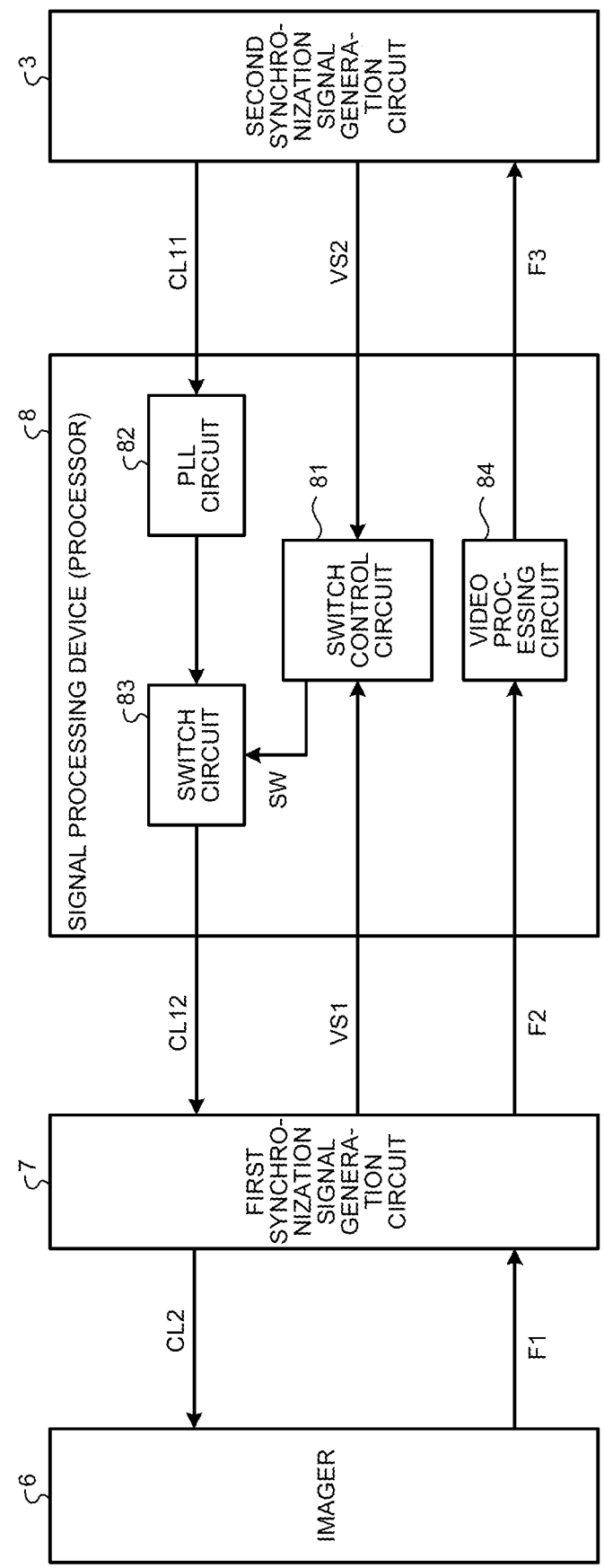
FIG. 2 is a block diagram illustrating a configuration of a main part of the endoscope system.

FIG. 2 is a block diagram illustrating a configuration of a main part of the endoscope system 1.

The imager 6 operates in accordance with a clock signal CL2 (FIG. 2). The clock signal CL2 is output from the first synchronization signal generation circuit 7, and is input to the imager 6 via the universal cord 23, the operating unit 22, and the insertion unit 21. Furthermore, the imager 6 captures an image of illumination light (subject image) emitted from the distal end portion 211 of the insertion unit 21 and reflected from the inside of the living body. Then, the imager 6 outputs an image signal F1 (FIG. 2) obtained by the imaging. Here, the imager 6 provides a change in a voltage level to the image signal F1 in order to cause the first synchronization signal generation circuit 7 to generate a synchronization signal VS1 (FIG. 2) from the image signal F1, for example, as in the technology described in U.S. Pat. No. 9,319,603 B2.

The imager 6 described above includes a charge coupled device (CCD), a complementary metal oxide semiconductor (CMOS), or the like that receives a subject image and converts the subject image into an electrical signal (analog signal).

The first synchronization signal generation circuit 7 includes an analog front end (AFE). In addition, the first synchronization signal generation circuit 7 includes a circuit that converts an analog signal into a digital signal (A/D conversion). Furthermore, the first synchronization signal generation circuit 7 generates the clock signal CL2 based on a clock signal CL12 (FIG. 2) input from the signal processing device 8. Then, the first synchronization signal generation circuit 7 outputs the clock signal CL2 to the imager 6. The clock signal CL2 corresponds to a clock signal. In addition, the first synchronization signal generation circuit 7 receives the image signal F1 output from the imager 6 and having passed through the insertion unit 21, the operating unit 22, and the universal cord 23. Then, the first synchronization signal generation circuit 7 performs a predetermined signal process (for example, A/D conversion or the like) on the image signal F1 to generate an image signal F2 (FIG. 2).

Further, the first synchronization signal generation circuit 7 generates the synchronization signal VS1 (FIG. 2) indicating timing at which the image signal F1 is transmitted for each frame based on a change in the voltage level of the input image signal F1, for example, as in the technique described in U.S. Pat. No. 9,319,603 B2. The synchronization signal VS1 corresponds to a first synchronization signal.

The signal processing device 8 includes a processor including at least one or more pieces of hardware such as a field programmable gate array (FPGA). As illustrated in FIG. 2, the signal processing device 8 includes a switch control circuit 81, a phase locked loop (PLL) circuit 82, a switch circuit 83, and a video processing circuit 84.

The switch control circuit 81 determines whether the synchronization signal VS1 output from the first synchronization signal generation circuit 7 and a synchronization signal VS2 generated by the second synchronization signal generation circuit 3 are synchronized. For example, when the pulse based on the synchronization signal VS1 and the pulse based on the synchronization signal VS2 rise at different times, the switch control circuit 81 determines that the synchronization signal VS1 and the synchronization signal VS2 are not synchronized. Then, when determining that the synchronization signal VS1 and the synchronization signal VS2 are not synchronized (cannot be synchronized), the switch control circuit 81 switches a switch signal SW (FIG. 2) output to the switch circuit 83 from the low level to the high level at the first timing. Further, the switch control circuit 81 switches it to the low level again at the second timing after the first timing.

Note that details of the first and second timings will be described in "Operation of endoscope system" described later.

A PLL circuit 82 is a frequency synthesizer, and generates the clock signal CL12 (FIG. 2) based on a clock signal CL11 (FIG. 2) output from the second synchronization signal generation circuit 3. Then, the PLL circuit 82 outputs the clock signal CL12 after passing through the switch circuit 83 to the first synchronization signal generation circuit 7.

The switch circuit 83 is provided on a line between the second synchronization signal generation circuit 3 and the first synchronization signal generation circuit 7, and the clock signal is transmitted on the line. In addition, the switch circuit 83 is turned off during a period in which it receives the high-level switch signal SW from the switch control circuit 81, and prohibits the input of the clock signal CL12 from the PLL circuit 82 to the first synchronization signal generation circuit 7. That is, the switch circuit 83 prohibits the input of the clock signal CL2 from the first synchronization signal generation circuit 7 to the imager 6. On the other hand, the switch circuit 83 is turned on during a period in which it receives the low-level switch signal SW from the switch control circuit 81, and permits the clock signal CL12 to be input from the PLL circuit 82 to the first synchronization signal generation circuit 7. That is, the switch circuit 83 permits the input of the clock signal CL2 from the first synchronization signal generation circuit 7 to the imager 6.

The video processing circuit 84 performs various types of image processes on the image signal F2 output from the first synchronization signal generation circuit 7 to generate an image signal F3.

The second synchronization signal generation circuit 3 includes a central processing unit (CPU), an FPGA, and the like. The second synchronization signal generation circuit 3 generates the clock signal CL1*l* and the synchronization signal VS2 (FIG. 2) indicating the timing at which the image signal F3 is acquired for each frame to output the signals to the signal processing device 8 (the PLL circuit 82 and the switch control circuit 81). In addition, the second synchronization signal generation circuit 3 performs various types of image processes on the image signal F3 output from the signal processing device 8 (video processing circuit 84). Then, the image based on the image signal after the execution of the various types of image processes is displayed on the display device 4.

Note that the synchronization signal VS2 described above corresponds to a second synchronization signal.

Operation of endoscope system Next, an operation of the endoscope system 1 will be described. Note that operations of the imager 6, the first synchronization signal generation circuit 7, the signal processing device 8, and the second synchronization signal generation circuit 3, which are main parts of the endoscope system 1, will be mainly described below.

Figure 3:
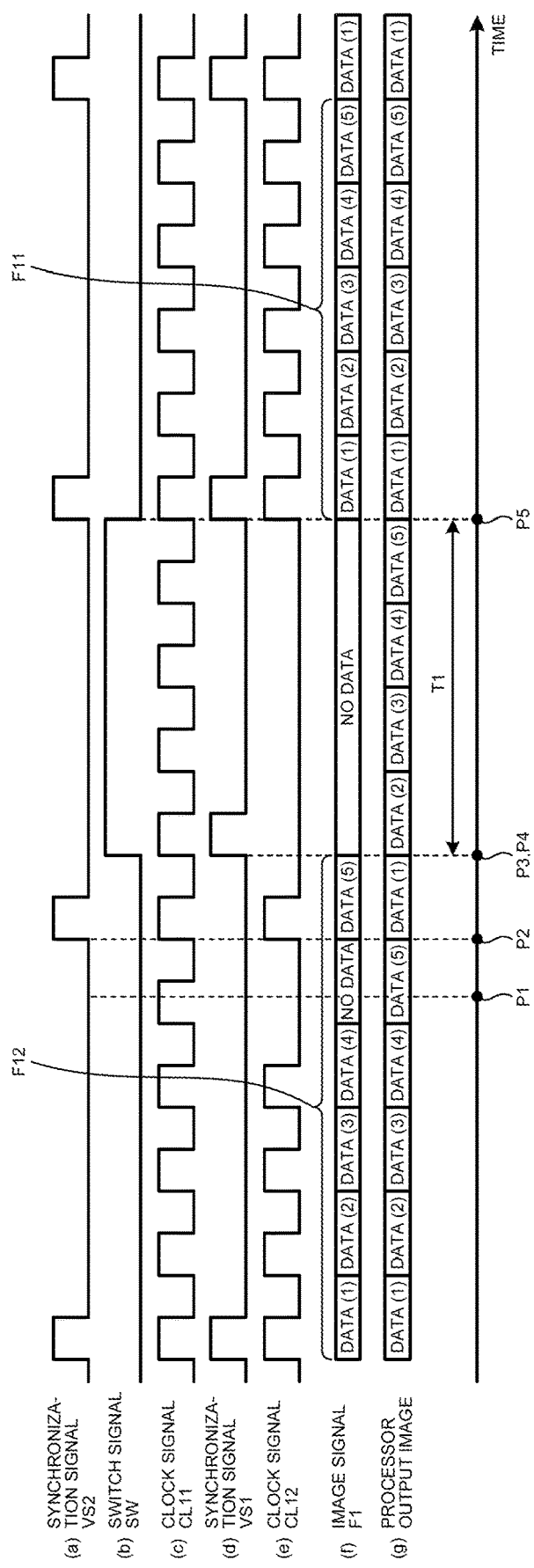
FIG. 3 is a time chart illustrating an operation of the endoscope system.

FIG. 3 is a time chart illustrating an operation of the endoscope system 1. Specifically, (a) to (g) in FIG. 3 illustrate the synchronization signal VS2, the switch signal SW, the clock signal CL11, the synchronization signal VS1, the clock signal CL12, the image signal F1, and a processor output image, respectively. Here, the processor output image is based on the synchronization signal VS2 indicating the timing at which the image signal F3 is acquired for each frame, and indicates the timing at which each data of the image signal F3 for the one frame is acquired. In FIG. 3, the image signal F3 for the one frame is composed of five pieces of data (data (1) to (5)). The data (1) means the first data for the one frame. The data (2) means the second data for the one frame. The data (3) means the third data for the one frame. The data (4) means the fourth data for the one frame. The data (5) means the last data for the one frame.

Hereinafter, it is assumed that a treatment instrument such as an electric scalpel or a snare is used at high output at time P1 (FIG. 3), and the clock signal CL2 or the image signal F1 is affected by disturbance from the treatment instrument. In (e) in FIG. 3, the pulse of the clock signal CL2 disappears due to the influence of the disturbance. In (f) in FIG. 3, the data of the image signal F1 is lost (described as "no data" in (f) in FIG. 3).

Here, the first synchronization signal generation circuit 7 detects a change in the voltage level of the image signal F1, thereby estimating which data of the image signal F1 for one frame is transmitted from the imager 6. Then, when the first synchronization signal generation circuit 7 estimates that the image signal F1 for one frame has been transmitted based on the change in the voltage level, the first synchronization signal generation circuit 7 starts a pulse based on the synchronization signal VS1. In the case described above, since the clock signal CL2 and the image signal F1 are affected by disturbance, a change other than the change in the voltage level generated by the imager 6 occurs in the image signal F1. Then, since the first synchronization signal generation circuit 7 detects a change other than the change in the voltage level generated by the imager 6, erroneous estimation is made. Therefore, the pulse based on the synchronization signal VS1 rises at time P3 (FIG. 3), which is shifted from time P2 (FIG. 3) at which the pulse based on the synchronization signal VS2 first rises after time P1 ((d) in FIG. 3). That is, the switch control circuit 81 determines that the synchronization signal VS1 and the synchronization signal VS2 are not synchronized (cannot be synchronized) at time P2.

Then, after time P2, the switch control circuit 81 switches the switch signal SW output to the switch circuit 83 from the low level to the high level at the first timing P4 ((b) in FIG. 3). After the first timing P4, the switch control circuit 81 switches the switch signal SW output to the switch circuit 83 to the low level again at the second timing P5 ((b) in FIG. 3).

Here, the first timing P4 is timing after time P2 and before the image signal F11 (F1 ((f) in FIG. 3) for the next one frame is output from the imager 6. In the first embodiment, the first timing P4 is timing at which the output of the image signal F12 (F1 ((f) in FIG. 3) for one frame output from the imager 6 at time P2 is completed.

The second timing P5 is timing at which the pulse based on the synchronization signal VS2 rises after the first timing P4. In the first embodiment, the second timing P5 is timing at which the pulse based on the synchronization signal VS2 rises "first" after the first timing P4.

As a result, the switch circuit 83 is turned off in a period T1 from the first timing P4 to the second timing P5, and prohibits the input of the clock signal CL12 from the PLL circuit 82 to the first synchronization signal generation circuit 7. That is, during the period T1, the switch circuit 83 is in the second state in which the input of the clock signal CL2 to the imager 6 is prohibited ((e) in FIG. 3. In addition, the switch circuit 83 is turned on after the second timing P5 and permits the clock signal CL12 to be input from the PLL circuit 82 to the first synchronization signal generation circuit 7. That is, after the second timing P5, the switch circuit 83 is in the first state in which the input of the clock signal CL2 to the imager 6 is permitted ((e) in FIG. 3).

Then, when the input of the clock signal CL2 is recovered, the imager 6 starts outputting the image signal F1*l* for one frame from the first data (data (1)) after the second timing P5. As a result, the first synchronization signal generation circuit 7 raises a pulse based on the synchronization signal VS1 at the second timing P5 based on the image signal F1*l*. That is, the synchronization signal VS1 and the synchronization signal VS2 can be synchronized at the second timing P5.

When the synchronization signal VS1 and the synchronization signal VS2 are synchronized (when the data of the image signal F1 ((f) in FIG. 3) and the data of the processor output image ((g) in FIG. 3) match), an appropriate image is displayed on the display device 4. On the other hand, when the synchronization signal VS1 and the synchronization signal VS2 are not synchronized (when the data of the image signal F1 ((f) in FIG. 3) and the data of the processor output image ((g) in FIG. 3) do not match), an appropriate image is not displayed on the display device 4.

According to the first embodiment described above, the following effects are obtained.

Figure 4:
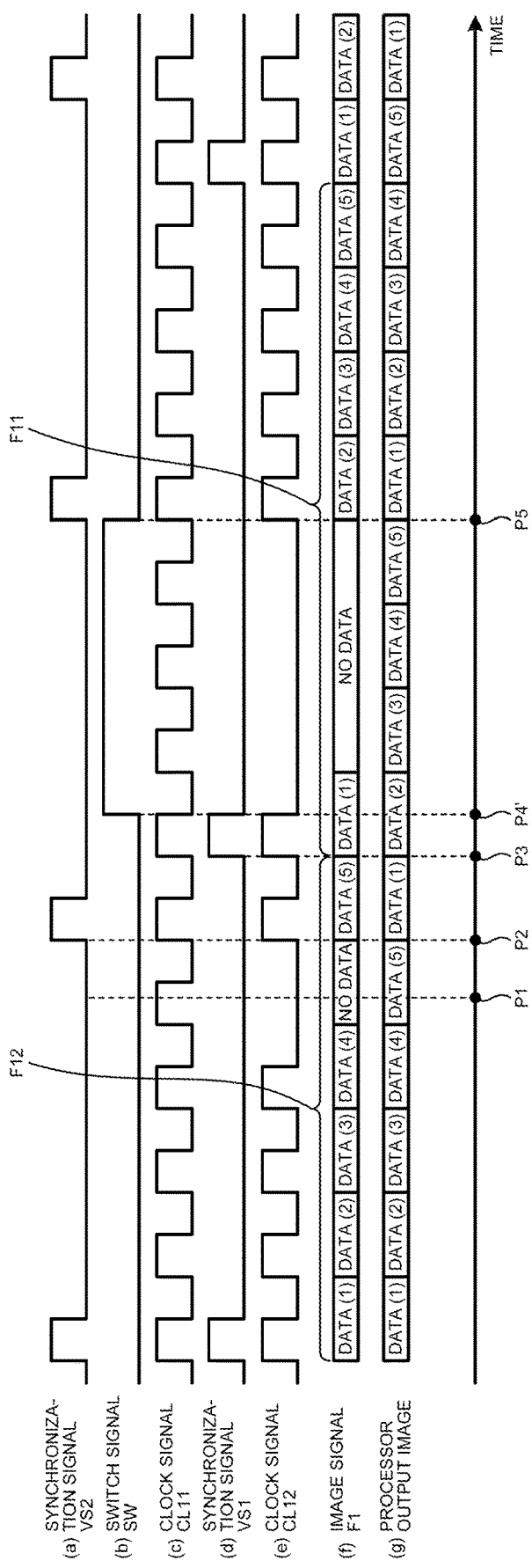
FIG. 4 is a view for describing effects of the first embodiment.
Figure 5:
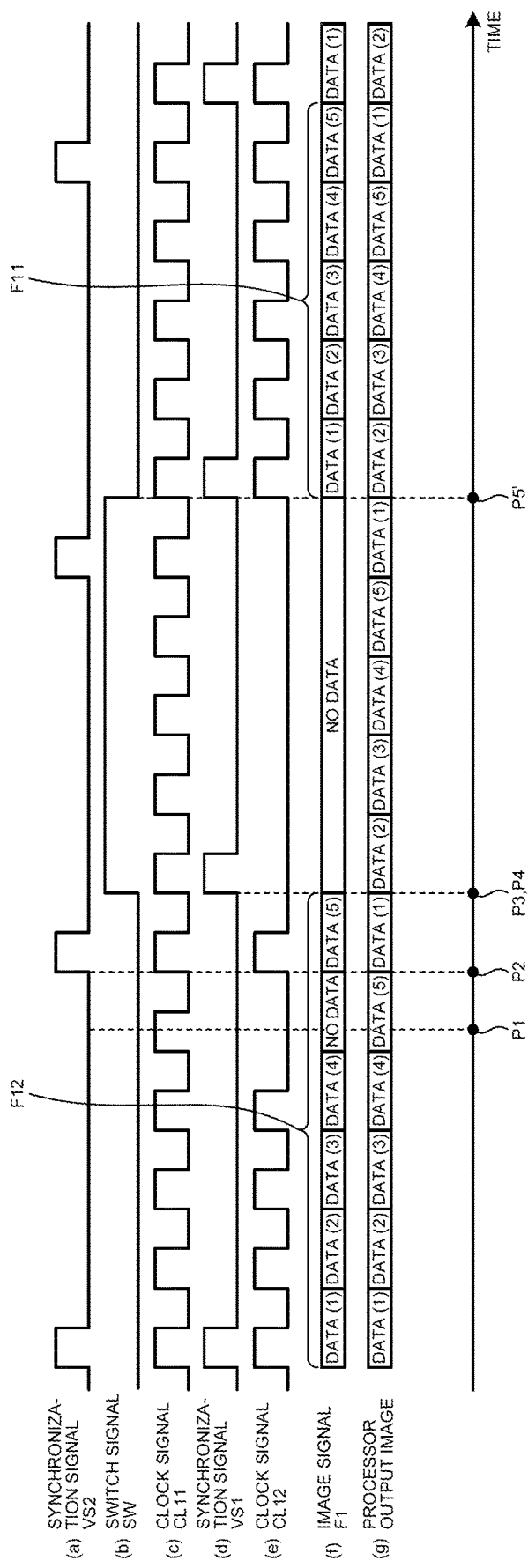
FIG. 5 is a view for describing effects of the first embodiment.

FIGS. 4 and 5 are diagrams illustrating effects of the first embodiment. Note that FIG. 4 is a time chart corresponding to that in FIG. 3, and illustrates a case where the timing at which the switch signal SW is switched from the low level to the high level after time P2 is set to the first timing P4' shifted from the first timing P4. FIG. 5 is a time chart corresponding to that in FIG. 3, and illustrates a case where the timing at which the switch signal SW is switched to the low level again after the first timing P4 is set to the second timing P5' shifted from the second timing P5.

Meanwhile, as described above, the first synchronization signal generation circuit 7 estimates which data of the image signal F1 for one frame is transmitted from the imager 6 based on only the change in the voltage level of the image signal F1. Therefore, after the synchronization deviation between the synchronization signal VS1 and the synchronization signal VS2 occurs due to the influence of the disturbance, the synchronization deviation is not eliminated by the lapse of time.

The signal processing device 8 according to the first embodiment temporarily switches the switch circuit 83 from the first state to the second state when the synchronization deviation occurs. That is, the synchronization deviation can be eliminated by temporarily stopping the operation of the imager 6. That is, an image based on the image signal F1 generated by the imager 6 can be appropriately displayed.

Here, it is assumed that, after time P2, the timing at which the switch signal SW is switched from the low level to the high level is shifted from the first timing P4 to the first timing P4' (FIG. 4) at which the image signal F1*l* for one frame has already started to be output from the imager 6.

In this case, even when the switch signal SW is switched to the low level again at the second timing P5 after the first timing P4', the image signal F1*i* for one frame has already started to be output before the operation of the imager 6 is stopped. Therefore, after the second timing P5, the data of the image signal F1 ((f) in FIG. 4) and the data of the processor output image ((f) in FIG. 4) do not match. That is, an appropriate image is not displayed on the display device 4.

In addition, it is assumed that, after the first timing P4, the timing at which the switch signal SW is switched to the low level again is shifted from the second timing P5 to the second timing P5' (FIG. 5) other than the timing at which the pulse based on the synchronization signal VS2 rises.

In this case, at the timing at which the image signal F1*l* for one frame is output, the data of the image signal F1 and the data of the processor output image do not match ((f) and (g) in FIG. 5). That is, an appropriate image is not displayed on the display device 4.

On the other hand, in the signal processing device 8 according to the first embodiment, after time P2, the switch signal SW is switched from the low level to the high level at the first timing P4, and after the first timing P4, the switch signal SW is switched to the low level again at the second timing P5. Therefore, after the second timing P5, the data of the image signal F1 ((f) in FIG. 3) and the data of the processor output image ((g) in FIG. 3) match, and an appropriate image can be displayed on the display device 4.

Specifically, the second timing P5 is timing at which the pulse based on the synchronization signal VS2 rises "first" after the first timing P4. Therefore, period T1 (period in which the image is not displayed on the display device 4) from the first timing P4 to the second timing P5 can be shortened, and the period in which the image is not displayed on the display device 4 can be shortened.

In addition, the imager 6 has a configuration in which a function of transmitting and receiving a synchronization signal is removed. Therefore, the imager 6 can be downsized, whereby the diameter of the insertion unit 21 provided with the imager 6 can be reduced.

Second Embodiment

Next, the second embodiment will be described.

In the following description, the same reference numerals are given to the same configurations as those of the first embodiment described above, and a detailed description thereof will be omitted or simplified.

Figure 6:
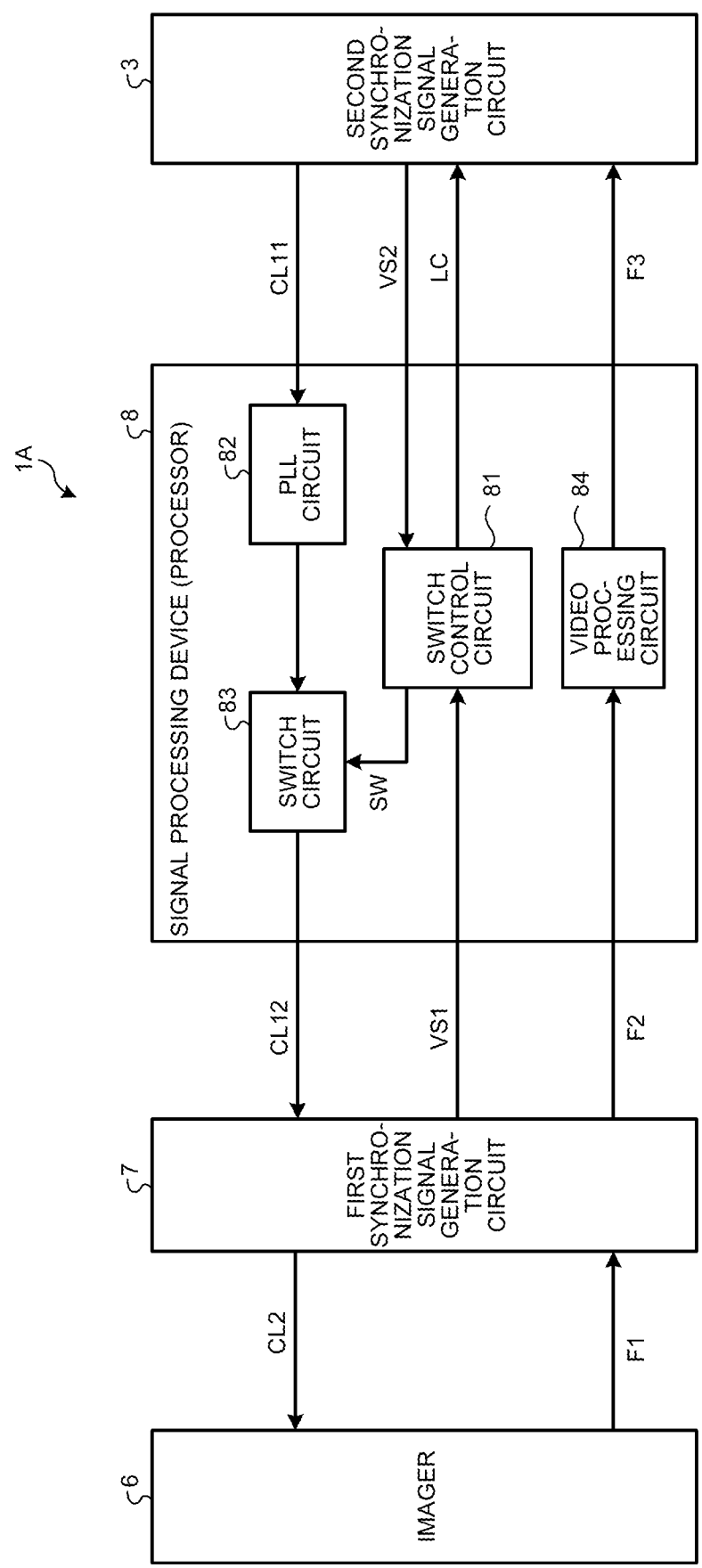
FIG. 6 is a block diagram illustrating a configuration of a main part of an endoscope system according to a second embodiment.

FIG. 6 is a diagram corresponding to FIG. 2 and is a block diagram illustrating a configuration of a main part of an endoscope system 1A according to the second embodiment.

In the endoscope system 1A according to the second embodiment, as illustrated in FIG. 6, the switch control circuit 81 in the endoscope system 1 (FIG. 2) described in the above-described first embodiment outputs a high-level light amount control signal LC to the second synchronization signal generation circuit 3 during the period T1 from the first timing P4 to the second timing P5. In a period other than the period T1, the switch control circuit 81 outputs a low-level light amount control signal LC to the second synchronization signal generation circuit 3. Then, the second synchronization signal generation circuit 3 controls the operation of the light source device 5 during the period T1 in which it receives the high-level light amount control signal LC, and sets an amount of light of the illumination light emitted from the light source device 5 to be lower than that in another period.

The second embodiment described above has the following effects in addition to the same effects as the first embodiment described above.

An image based on the image signal F1*l* for one frame is an image signal generated as a result of excessive exposure during the period T1. Therefore, the image based on the image signal F1*l* has relatively high brightness.

Here, in the endoscope system 1A according to the second embodiment, the amount of illumination light during the period T1 is set to be lower than that in another period. Therefore, the brightness of the image based on the image signal F11 can be set to an appropriate brightness, and an appropriate image can be displayed.

Third Embodiment

Next, the third embodiment will be described.

In the following description, the same reference numerals are given to the same configurations as those of the first embodiment described above, and a detailed description thereof will be omitted or simplified.

FIG. 7 is a diagram corresponding to FIG. 2 and is a block diagram illustrating a configuration of a main part of an endoscope system 1B according to the third embodiment.

In the endoscope system 1B according to the third embodiment, as illustrated in FIG. 7, an attenuation circuit 85 is added to the signal processing device 8 in the endoscope system 1 (FIG. 2) described in the above-described first embodiment.

Here, the switch control circuit 81 according to the first embodiment outputs a high-level gain signal G1 (FIG. 7) to the attenuation circuit 85 in a period from the second timing P5 until the pulse based on the synchronization signal VS2 rises next. In a period other than this period, the switch control circuit 81 outputs a low level gain signal G1 to the attenuation circuit 85.

The attenuation circuit 85 is provided on a line between the first synchronization signal generation circuit 7 and the second synchronization signal generation circuit 3, and an image signal is transmitted on the line. In addition, the attenuation circuit 85 adjusts the brightness of the image based on the image signal F2 by multiplying the pixel value of each pixel in the image signal F2 output from the first synchronization signal generation circuit 7 by the gain. Then, the attenuation circuit 85 outputs the image signal F2 after the brightness is adjusted to the video processing circuit 84. Specifically, the attenuation circuit 85 multiplies the pixel value of each pixel in the image signal F2 by a first gain during a period in which it receives the low level gain signal G1 from the switch control circuit 81. On the other hand, the attenuation circuit 85 multiplies the pixel value of each pixel in the image signal F2 by a second gain smaller than the first gain during a period in which it receives the high-level gain signal G1 from the switch control circuit 81.

According to the third embodiment described above, the following effects are obtained in addition to the same effects as those of the first embodiment described above.

The signal processing device 8 according to the third embodiment makes the image based on the image signal F2 (image signal F11) for one frame input during the period from the second timing P5 until the pulse based on the synchronization signal VS2 rises next darker than the images based on the image signals F2 for another frame. Therefore, as in the second embodiment described above, it is possible to set the brightness of the image based on the image signal F11 to an appropriate brightness and display an appropriate image.

Other Embodiments

Although the embodiments for carrying out the disclosure have been described so far, the disclosure should not be limited only by the above-described first to third embodiments.

In the first to third embodiments described above, the switch control circuit 81 determines whether the synchronization signal VS1 and the synchronization signal VS2 are synchronized. When determining that the synchronization is not established, the switch control circuit 81 switches the switch signal SW output to the switch circuit 83 from the low level to the high level at the first timing P4. However, the switch control circuit 81 may not execute the determination.

For example, in a case where a user such as an operator determines that an appropriate image is not displayed on the display device 4, the user performs an operation on an input unit (not illustrated) constituting the endoscope systems 1, 1A, and 1B. Then, after the operation, the switch control circuit 81 switches the switch signal SW output to the switch circuit 83 from the low level to the high level at the first timing P4.

That is, the function of determining whether the synchronization signal VS1 and the synchronization signal VS2 are synchronized may be removed from the switch control circuit 81 (signal processing device 8).

In the above-described first to third embodiments, the signal processing device 8 is configured separately from the second synchronization signal generation circuit 3, but the disclosure is not limited thereto, and it may be mounted in the second synchronization signal generation circuit 3. Similarly, the signal processing device 8 is configured separately from the first synchronization signal generation circuit 7, but the disclosure is not limited thereto, and it may be mounted in the first synchronization signal generation circuit 7.

In addition, the switch circuit 83 may be provided on a line that transmits the clock signal CL2 between the imager 6 and the first synchronization signal generation circuit 7 to permit or prohibit the input of the clock signal CL2 to the imager 6.

In the third embodiment described above, the attenuation circuit 85 is provided in the signal processing device 8, but the disclosure is not limited thereto, and the attenuation circuit 85 may be provided on a line that transmits the image signal F1 between the imager 6 and the first synchronization signal generation circuit 7 to adjust the brightness of the image based on the image signal F1.

FIG. 8 is a diagram illustrating a modification of the first to third embodiments. FIG. 8 is a time chart corresponding to that in FIG. 3. Specifically, (a) to (h) in FIG. 8 illustrate the synchronization signal VS2, the switch signal SW, the clock signal CL11, the synchronization signal VS1, the clock signal CL12, the image signal F1, the processor output image, and the image signal F3, respectively. Note that FIG. 8 illustrates a case where the timing at which the switch signal SW is switched from the low level to the high level is set to the first timing P4" shifted from the first timing P4 after time P2. In addition, FIG. 8 illustrates a case where the timing at which the switch signal SW is switched to the low level again after the first timing P4 is set to the second timing P5" shifted from the second timing P5.

In the above-described first to third embodiments, the timing at which the switch signal SW is switched from the low level to the high level is set to the first timing P4, and the timing at which the switch signal SW is again switched to the low level is set to the second timing P5, but the disclosure is not limited thereto.

For example, when a data storage function is added to the video processing circuit 84, an appropriate image can be displayed on the display device 4 even when the first and second timings (in the example of FIG. 8, the first and second timings P4" and P5") other than the first and second timings P4 and P5 are set.

Specifically, when the switch signal SW is at the low level, the video processing circuit 84 outputs the processed image signal F3 as it is to the second synchronization signal generation circuit 3 ((f) and (h) in FIG. 8). On the other hand, when the switch signal SW is at the high level, the video processing circuit 84 constantly monitors the image signal F2 input from the first synchronization signal generation circuit 7.

Further, when the image signal F2 is input during the monitoring, the video processing circuit 84 stores the image signal F2. In the example of (h) in FIG. 8, since the data (1) of the image signal F2 is input after the first timing P4", the data (1) is stored. Then, the video processing circuit 84 outputs the data (1) stored at the timing P5 at which the pulse based on the synchronization signal VS2 first rises after the first timing P4" to the second synchronization signal generation circuit 3. In addition, the switch control circuit 81 switches the switch signal SW from the high level to the low level at the second timing P5" at which the output of the data (1) is completed. As a result, after the second timing P5", the data of the image signals F1 and F3 ((f) and (h) in FIG. 8) and the data of the processor output image ((g) in FIG. 8) match, and an appropriate image can be displayed on the display device 4.

According to the signal processing device, the signal processing method, and the endoscope system according to the disclosure, it is possible to display an appropriate image.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A signal processing device comprising:
   a processor comprising at least one or more pieces of hardware, the processor being configured to:
   switch to one of a first state in which an input of a clock signal for operating an imager to the imager is permitted and a second state in which the input of the clock signal to the imager is prohibited, and
   temporarily switch from the first state to the second state when a first synchronization signal output from a first synchronization signal generation circuit and a second synchronization signal output from a second synchronization signal generation circuit are not synchronized.

2. The signal processing device according to claim 1, wherein
   the processor is further configured to
   determine whether the first synchronization signal and the second synchronization signal are synchronized, and
   temporarily switch from the first state to the second state when it is determined that the first synchronization signal and the second synchronization signal are not synchronized.

3. The signal processing device according to claim 2, wherein
   the processor is further configured to
   determine that the first synchronization signal and the second synchronization signal are not synchronized when a pulse based on the first synchronization signal and a pulse based on the second synchronization signal rise at different times.

4. The signal processing device according to claim 1, wherein
   after the first synchronization signal and the second synchronization signal are not synchronized, the processor is further configured to switch from the first state to the second state before an image signal of a next one frame is output from the imager.

5. The signal processing device according to claim 4, wherein
   after switching from the first state to the second state, the processor is further configured to switch to the first state at timing at which a pulse based on the second synchronization signal rises.

6. The signal processing device according to claim 5, wherein
   after switching from the first state to the second state, the processor is further configured to switch to the first state at timing at which a pulse based on the second synchronization signal first rises.

7. The signal processing device according to claim 1, wherein
   the processor is further configured to darken an image based on an image signal for at least one frame output from the imager after switching from the first state to the second state, and switching to the first state again.

8. The signal processing device according to claim 7, wherein
   the processor is further configured to multiply the image signal by a gain that is a smaller one of two gains to be multiplied to the image signal.

9. The signal processing device according to claim 8, wherein
   the processor is further configured to multiply an image signal output from the first synchronization signal generation circuit by the smaller one of the two gains.

10. The signal processing device according to claim 8, wherein
    the processor is further configured to multiply an image signal output from the imager and input to the first synchronization signal generation circuit by the smaller one of the two gains.

11. The signal processing device according to claim 1, wherein
    when switching from the first state to the second state, the processor is further configured to start storage of an image signal output from the imager.

12. The signal processing device according to claim 11, wherein
    when switching from the first state to the second state and thereafter a pulse based on the second synchronization signal first rises, the processor is further configured to start output of the stored image signal.

13. An endoscope system comprising:
    an endoscope configured to be inserted into a subject; and
    a processor comprising at least one or more pieces of hardware, the processor being configured to:
    switch to one of a first state in which an input of a clock signal for operating an imager to the imager is permitted and a second state in which the input of the clock signal to the imager is prohibited, and
    temporarily switch from the first state to the second state when a first synchronization signal output from a first synchronization signal generation circuit and a second synchronization signal output from a second synchronization signal generation circuit are not synchronized.

14. The endoscope system according to claim 13, further comprising:
    a light source configured to emit illumination light with which the subject is irradiated, wherein
    the processor is further configured to
    control an operation of the light source during a period in which a state is switched to the second state to set an amount of light of the illumination light in the period to be lower than an amount of light in another period.

15. A signal processing method executed by a processor comprising at least one or more pieces of hardware, the signal processing method comprising:

switching to one of a first state in which an input of a clock signal for operating an imager to the imager is permitted and a second state in which the input of the clock signal to the imager is prohibited; and temporarily switching from the first state to the second state when a first synchronization signal output from a first synchronization signal generation circuit and a second synchronization signal output from a second synchronization signal generation circuit are not synchronized.

* * * * *